United States Patent [19]

Dorf et al.

[11] 4,442,934
[45] Apr. 17, 1984

[54] GLASS CONTAINER INSPECTION HANDLING SYSTEM

[75] Inventors: Arthur L. Dorf; Sam Lovalenti; John J. Pezzin, all of Toledo, Ohio; Darius O. Riggs, Ottawa Lake, Mich.

[73] Assignee: Owens-Illinois, Inc., Toledo, Ohio

[21] Appl. No.: 444,278

[22] Filed: Nov. 24, 1982

Related U.S. Application Data

[62] Division of Ser. No. 203,024, Nov. 3, 1980, Pat. No. 4,378,493.

[51] Int. Cl.³ .............................................. B65G 29/00
[52] U.S. Cl. ................................... 198/344; 198/475; 198/481; 198/482; 198/484
[58] Field of Search ............... 198/344, 394, 468, 475, 198/481, 482, 483, 484; 209/522, 523, 524, 525, 526, 527, 528, 529; 250/223 B

[56] References Cited

U.S. PATENT DOCUMENTS

| | | | |
|---|---|---|---|
| 2,880,845 | 4/1959 | Carter | 198/394 |
| 3,313,409 | 4/1967 | Johnson | 209/525 |
| 3,710,937 | 1/1973 | Cook | 209/523 |

*Primary Examiner*—James L. Rowland
*Attorney, Agent, or Firm*—Gerald T. Welch; Myron E. Click

[57] ABSTRACT

Apparatus for inspecting glass containers in which an indexing starwheel moves a plurality of containers in series through a plurality of positions or stations where the containers are physically and optically examined.

One station, or position, is described in detail as the position where a glass container that is in a vertical position is rotated about its vertical axis by engagement of the finish thereof with a driven wheel. Rotating worm means move the bottles into and out of the handling system and serve as means to time the bottle movements. A mechanism at the exit position assists the bottles out of the starwheel. At the station where the sidewall of the bottles is to be inspected, a light source in the form of a tall housing is positioned in a vertical, annular recess of the starwheel. Additionally, the starwheel is made such that individual containers are contacted by rollers supported from the starwheel and at the sidewall inspection station the container is held in the starwheel, in engagement with the lower rollers, by a side-engaging biased roller. The manner of holding and rotating the bottle is such that a vertical sidewall section of the container is unobstructed, both from the viewpoint of outwardly directed illumination, and view by a camera positioned radially outward of the container.

9 Claims, 7 Drawing Figures

GLASS CONTAINER INSPECTION HANDLING SYSTEM

This is a division of application Ser. No. 203,024 filed Nov. 3, 1980, now U.S. Pat. No. 4,378,493.

BACKGROUND OF THE INVENTION

In the operation of apparatus for the inspection of glass containers, it is assumed that automatic inspection may be made better than manual or visual inspection by operators. This invention relates to an apparatus for inspecting glassware and in particular to apparatus for inspecting the sidewall of hollow glass containers for defects which are of an optically distinguishable character. As might be expected, in the manufacture of blown hollow glass containers it sometimes happens that the sidewall of the container, that is that portion of the container below the finish or neck of the bottle and above the curved heel and bottom of the bottle, has defects which would affect the performance of the container in service. It is important that every blown glass container have its sidewall, among other portions of the container, inspected for defects and it would be a great advantage if these containers could be inspected at high speeds with a high degree of reliability so that when a container passes the inspection, it would be positively free of defects in the sidewall thereof.

In the past, there have been inspection devices which would inspect containers for defects in the finish portion such as "line-over-finishes," "checks" (both vertical and horizontal), "seeds" and "blisters." Further, there have been bottom and heel check detectors which operate on the principle of optical reflectance or refraction. Furthermore, there have been inspection devices which inspected the containers to ensure that their height is correct, that the finish of the bottle is free of "dips and warps" and that the finish of the container not be cocked or out of alignment with the general central vertical axis of the container. Such an inspection apparatus may be found by reference to U.S. Pat. No. 3,313,409 issued to J. R. Johnson and assigned to the Assignee of the present application.

The disclosure of this U.S. Pat. No. 3,313,409 is incorporated herein by reference thereto. A reading of this patent will indicate that there are four inspection stations in the inspection device which are labeled II, III, IV and V. While the present disclosure is directed specifically to the inspection of the sidewall area of a glass container, the invention should be considered in its broader sense as a system for inspecting at any one of the stations as depicted in the above-referred-to Johnson patent.

In the present disclosure, only one station of the inspection machine is disclosed in detail, inasmuch as this is the station in which the containers are to be inspected for sidewall defects by the system of the invention. While the Johnson patent is dealing with what would appear to be fairly small size containers, the general principle of operation of the device is one which would readily lend itself to the handling of a plurality of larger size containers through a series of inspection stations by having the ware brought to the machine with the turret or head then being indexed through approximately a 45° angle of rotation. This indexing motion carries the containers in the present invention through five inspection positions with a first position in advance of the first inspection station being in alignment with a conveyor that bring the bottles into the machine followed by five inspection positions and then followed by an exit position. Intermediate the exit position and the entrance position is what is termed a "reject position" or zone where bottles which have been sensed as defective by the apparatus, are retained in the apparatus so as to be cleared from the apparatus turret at this intermediate position. At this position, a cullet bin or other defective container disposal chute may be positioned. Frequently, these bottles which are rejected are returned, by a suitable coveying system, to the forming area where the forming operator may examine the container and in this way determine what might be an appropriate change to the process or to the machinery being used to correct any ongoing or long-term defect which is being produced. As in many manufacturing processes, defects sometimes crop up without any apparent reason, while in other instances a defect may appear and continue to appear through a period of production. These types of recurring defects are those which the present invention is most capable of determining and alerting the operators to the situation. Furthermore, any glass container which is made with any kind of a structural defect which might affect its performance in the market place is gauged, inspected and discarded when such a defect is detected, no matter for what reason the defect may have been produced.

It will be noted that the starwheel or indexing mechanism head of the prior art shown in the above-mentioned U.S. Pat. No. 3,313,409 consists generally of a pair of flat plates having notches formed in the periphery thereof within which containers to be inspected are serially placed. The starwheel of the present invention is considerably modified and improved for the purpose of handling containers in such a manner that they may be successfully inspected by illumination of the sidewall of the container to its full height. This is something which has not been easily achievable in prior devices where multiple inspections are being made. It has also been the practice in the past to move containers down a conveyor and, in effect, use a pair of TV cameras looking at the bottle at two angles in an effort to determine whether or not a container is of an acceptable appearance or shape. One serious drawback with such a device has been the inability to completely examine 360° of the container sidewall without distortion being injected into the system due to the fact that the edges of the container produce optical refractance and reflectance aberrations in the images viewed by the cameras.

With the foregoing in view, it is an object of the present invention to provide apparatus which is capable of moving glass containers through a series of inspection positions where various types of inspection may be carried out, with one of the positions being the location of a novel optical sidewall inspection device. Such sidewall inspection device comprises a source of illumination which will cover substantially the full height of the container and illuminate a vertical section of the sidewall from behind. Further, the source of illumination is variable in its intensity to provide greater illumination for containers that are formed of colored glass such as "amber," and to vary the intensity of the light at selected areas of the bottle depending on the shapes thereof.

The illuminated sidewall is viewed by a camera that is mounted outboard of the handling system. The camera is composed of a linear array of photosensitive devices onto which the illuminated image of the sidewall section is focused, with the array being scanned electronically and with the outputs being processed by microprocessor.

It is a further object of the invention to provide a container handling system capable of high speed operation and smooth handling of containers into and out of the indexing head or starwheel. The invention further consists of an improved starwheel construction which will permit rotation of a container at the sidewall inspection station without blocking the view of the camera and a novel mechanism to assist the movement of the containers out of the starwheel at the exit position.

Other and further objects will be apparent from the following detailed description taken in conjunction with the accompanying drawings.

SUMMARY OF THE INVENTION

Apparatus for inspecting the sidewall of transparent containers for optically detectable defects by having the container moved into an inspection position and rotated about its vertical axis. At the inspection position is located a stationary light source of sufficient height to illuminate substantially the full height of the container being inspected. The means for handling and rotating the container is such that it does not block the back illumination of the container by the light source which is formed of a plurality of lamps behind a diffusing plate. A camera with a vertical, linear array of light-responsive pickups is positioned so that it may view the illuminated vertical portion of the back-lighted front wall of the container being rotated and means are provided for monitoring the intensity of the light source and for handling a series of containers into and out of the inspection position.

Figure 1:
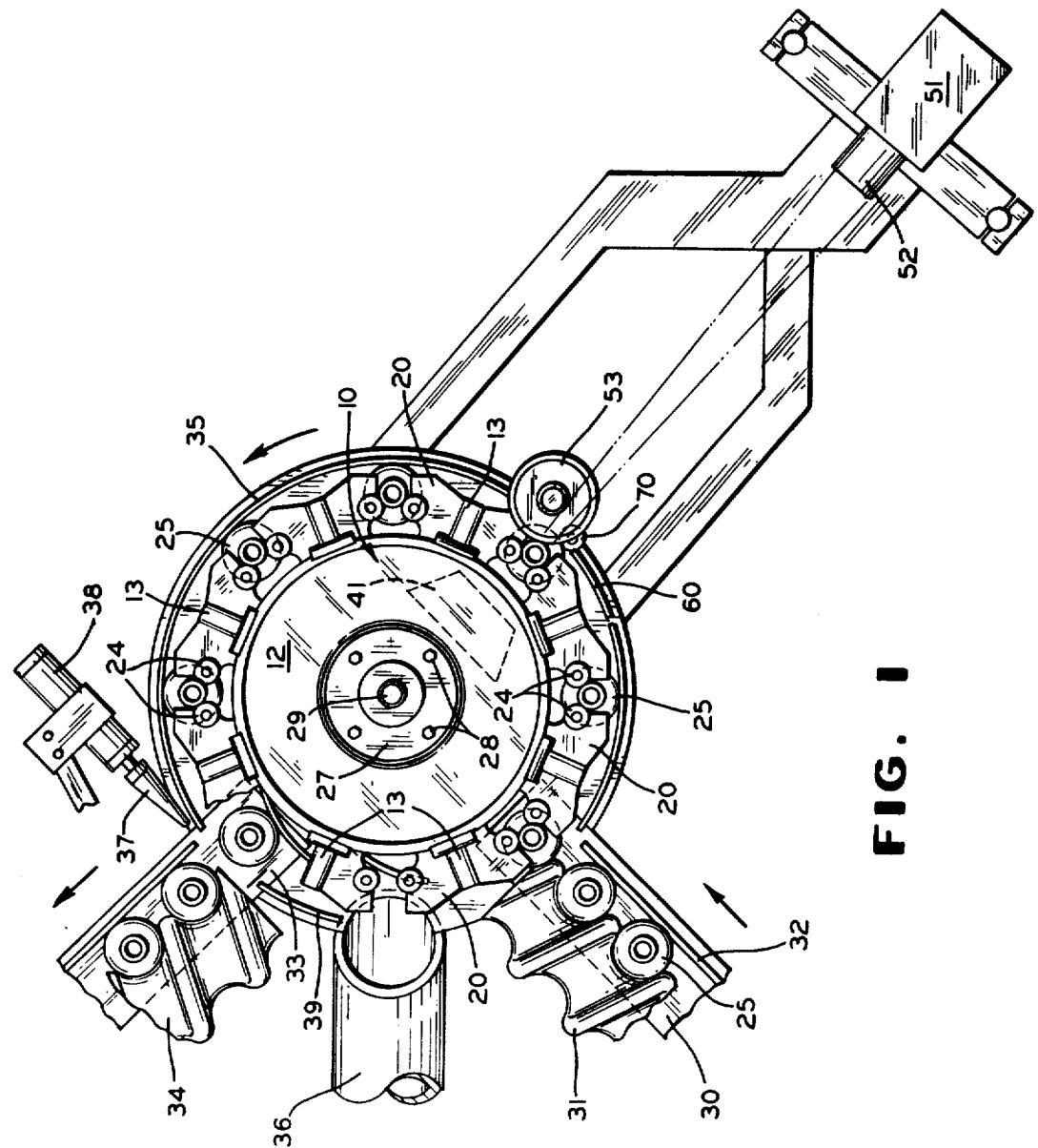
FIG. 1 is a top plan view of the apparatus of the invention.

The various aspects of the invention will be described in detail with an overall view being given in a general bottle handling section followed by a sidewall inspection section which will include a detailed description of a container-illuminating system. Further, the container exit position of the starwheel will be disclosed in light of the mechanism shown in the drawings.

DETAILED DESCRIPTION OF THE DRAWINGS

GENERAL BOTTLE HANDLING

Figure 4:
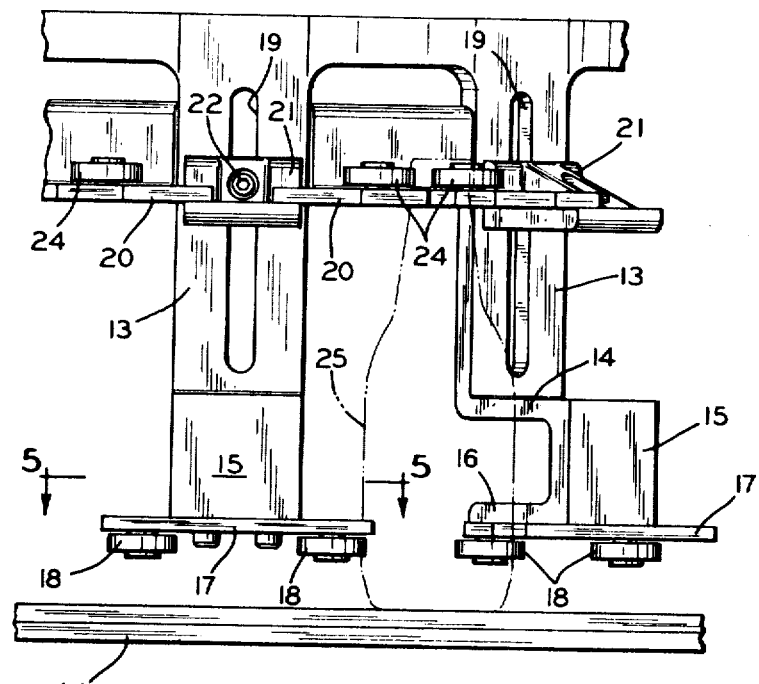
FIG. 4 is a side elevational view of a portion of the container supporting hub of the invention.
Figure 5:
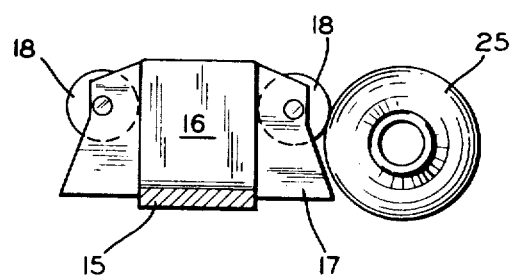
FIG. 5 is a view taken at line 5—5 of FIG. 4.

With particular attention to FIG. 1, there is shown, in plan view, a bottle inspection system for handling containers through a series of potential inspection positions and for determining the optical characteristics of the sidewall region of glass containers specifically at one position. Generally, the apparatus of FIG. 1 and the inspection system thereof is of a similar character to that described in U.S. Pat. No. 3,313,409, and consists of a starwheel, generally designated 10, in FIGS. 1-3. The starwheel 10, in effect, is formed of a generally cylindrical hub 11 having a radially outwardly, extending portion 12 to which are integrally formed downwardly extending arms 13 at spaced intervals about the periphery of the horizontally extending portion 12 of the hub 11. The downwardly extending arms 13, adjacent their lowermost portion, are provided with horizontally extending ledges 14 which extend outwardly to a radial extent at which point there is connected a downwardly extending arm extension 15. The downwardly extending extension 15 in turn has an inwardly extending horizontal ledge 16 formed thereto. The two ledges 14 and 16, along with the extension 15, in effect form a recess in the arm 13. The inwardly extending ledges 16 on the arms 13, of which there are 8 in the present apparatus, serve as mounts for plates 17 which are attached to the lower surface thereof. Each plate 17 extends horizontally outward from the sides of the ledge 16 to which it is attached and each plate carries a pair of bottle-engaging rollers 18, as best shown in FIG. 5. The arms 13 extend downwardly to such an extent that the lower ends thereof are below the center of gravity of the bottles or containers being handled. The rollers 18 which engage the bottles therefore engage the bottles below the center of gravity thereof. The downwardly extending arms 13 are provided with a vertically elongated slot 19 therein, the slot 19 serving as an adjustable mounting means for bifurcated plates 20. The plates 20 actually extend between adjacent arms 13. Each arm is provided with an angle bracket 21 which may be adjustably clamped to the arm 13 by suitable fasteners such as bolt 22 as shown in FIG. 4. The bolt 22 will extend through the vertical slot 19 and have a nut or other suitable threaded member on its opposite end. Loosening of the bolt 22 would permit vertical adjustment of the bracket 21 relative to the arm 13.

Figure 2:
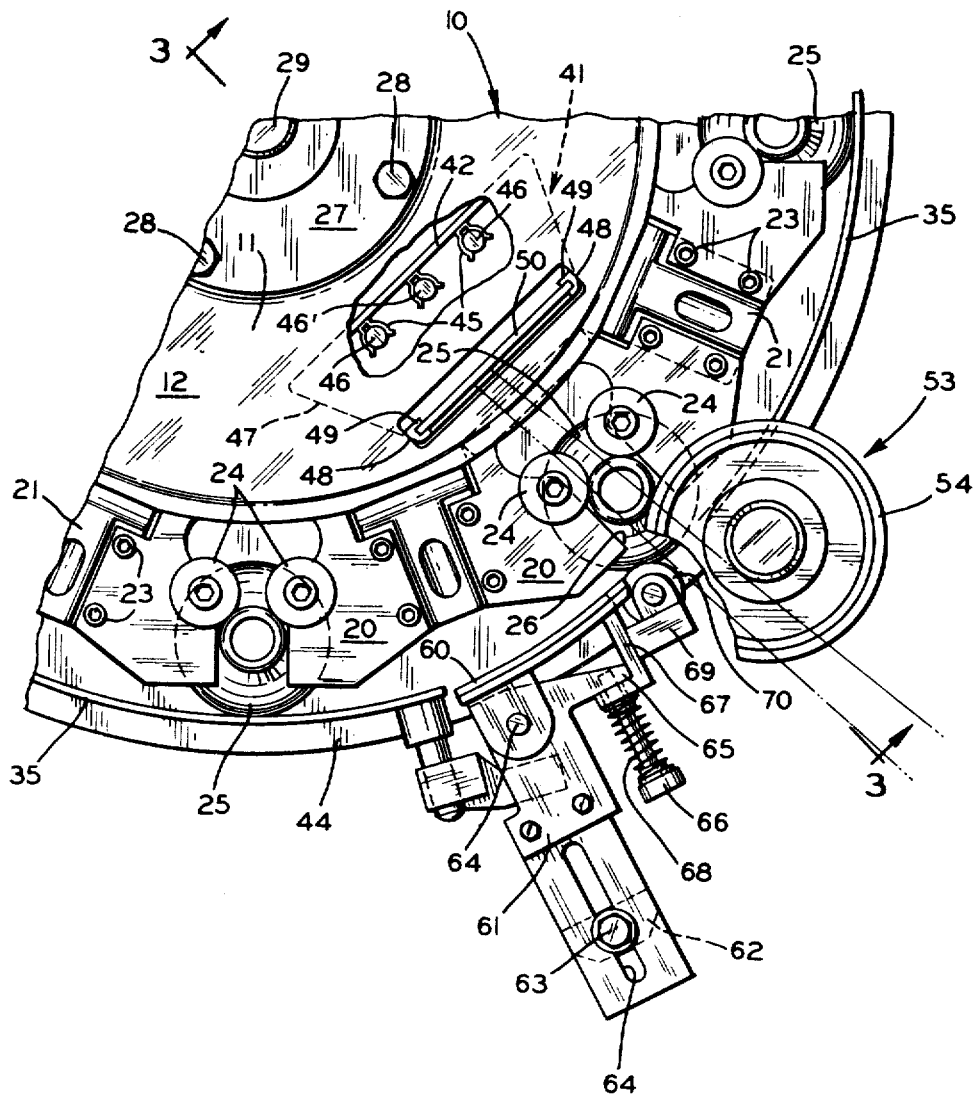
FIG. 2 is a plan view of the inspection of FIG. 1 on an enlarged scale.

As previously stated, the bracket 21 serves as a mounting platform for the bifurcated plates 20. It should be understood that each plate 20 is connected to a bracket 21 carried by adjacent arms. The mounting of the plate 20 to the bracket 21 may be by way of bolts 123, as shown in FIG. 2. Each plate 20 carries a pair of rollers 24. The rollers 24 are adapted to engage the "finish" or threaded neck portion of a glass container 25. The container 25 is shown in phantom line in FIGS. 3 and 4 and in full line in FIGS. 1 and 2. It should be pointed out that the plates 20 have a cut-out portion in the center thereof when looking in plan view with the forward portion, designated 26, being of a size such that the neck of a bottle will fit in the gap formed thereby, while the cut-out portion closest to the hub 11 is cut out to a greater degree and greater height for the purpose of permitting illumination of the bottle as will be later explained. Toward the rear portion of the cut-out 26 are mounted the two neck-engaging rollers 24. As can be seen in FIG. 2, the rollers 24 are equidistant from a plane passing through the center of the container positioned at the station shown in FIG. 2.

The hub 11 of the starwheel 10 is connected to a circular plate 27 by bolts 28. The circular pate 27 in turn is fastened to the upper end of a drive shaft 29. The drive shaft 29 is connected to a suitable indexing drive which will turn the drive shaft and the hub or starwheel connected thereto through a 45° angle of rotation during each indexing movement thereof.

With reference to FIG. 1, containers 25 are brought to the inspection device in an upright position on a conveyor 30. The conveyor 30 is moving in the direction of the arrow adjacent thereto and containers 25, as they approach the inspection device or the starwheel 10, are engaged by a screw 31. The screw 31 will be rotated at a preselected speed in a clockwise direction thus effecting the advancing movement of the containers 25 toward the center axis of the starwheel 10. The containers are confined to the threads of the screw by a guide rail 32. The timing of the screw is such that a container is brought into and becomes engaged by the starwheel 10 and the rollers 24 and 18 which are positioned at each station of the starwheel at predetermined intervals. Indexing of the starwheel will carry the container which has been positioned in the confines or "pocket" of the starwheel to the next adjacent position by indexing of the starwheel in a counter-clockwise direction. In this fashion, containers are, one by one, moved through a series of five inspection stations, only one of which is of specific concern in the present invention and which is illustrated in greater detail in FIGS. 2 and 3. The starwheel 10, it should be noted, handles the containers through the series of five inspection stations and when the containers arrive at the location of an exit conveyor 33, the containers will be assisted in leaving the pocket of the starwheel so as to become engaged by a screw 34 which is being rotated in a counter-clockwise direction to effect removal of the containers from the starwheel. Again the screw 34 is driven at a slightly greater velocity than the velocity of the conveyor 33. While the threads on the screw 34 are shown as symmetrical, they need not be of a regular pitch, but may have a greater separation distance as the screw becomes farther removed from the location of the starwheel 10. This is sometimes preferred when clearing the inspection device and for spacing containers on the exit conveyor.

It should be noted that the containers, as they are moved through the plurality of inspection stations, which are five in number between the entrance conveyor 30 and the exit conveyor 33, are held within the confines of the pockets in the starwheel by side-engaging rails 35 that are at a height which will render the containers fairly stable as they are moved laterally. Rails 35 are interrupted, obviously, at the entrance conveyor and at the exit conveyor so that the bottles may enter and exit from the starwheel. Furthermore, the rail 35 is not present at a portion of the distance between the exit conveyor and the entrance conveyor, since this is the zone where defective containers may be rejected by being positioned into a chute 36. In the event, during any of the inspections that may be carried out at the five stations where the containers are indexed to and between a defective bottle is determined to be present, a plunger 37 will be positioned by a cylinder 38 connected thereto to move into position to prevent the defective container from leaving the starwheel during that period when the starwheel is stationary and positioned in alignment with the exit conveyor 33. It can be seen that upon indexing of the starwheel with the container still retained adjacent the exit position by the plunger 37, that the starwheel will carry the defective container to the area of the disposal chute 36 and thus be discarded from the line of ware being inspected. Immediately after initial indexing movement of the starwheel has been sufficient to carry the defective container into engagement with the portion 39 of the guard rail, the plunger 37 will be retracted by the cylinder 38.

SIDEWALL INSPECTION

With specific reference now to FIGS. 2 and 3, a detailed description of the sidewall inspection system will be given.

The configuration of the starwheel is such that an annular, upstanding, recess 40 is provided therein within which serves as the location for an illuminating means generally designated 41. The illuminating means comprises a generally flat, vertically positioned panel 42 bolted to an angle bracket 43. The angle bracket 43 is supported from a horizontal, generally circular table 44. The panel 42 carries a plurality of fuse clips 45 in an array of three vertical columns with five individual clip pairs in each column. Each clip supports a lamp 46. The lamp 46 is a tubular bulb within which a vertically positioned filament is carried. These lamps are commercially available from General Electric and designated Style T-3, Lamp 211-2.

As can best be seen from FIG. 2, the lamps are positioned within a generally trapezoidally-shaped housing having sidewalls 47. The sidewalls 47, at their forward ends 48, are provided with vertical channels 49 within which a light-diffusing plate 50 is positioned in overlying relationship to all of the fifteen lamps. An opening is provided in the portion 12 of the starwheel 10 to provide access to the diffuser plate from above, to permit elevation of the diffusing plate, when desired, for the purpose of replacing lamps which may burn out during the operation of the device.

It should be noted that the illuminating means 41 extends below the table 44 such that the lowestmost lamps will provide full height illumination to the front side of a container positioned as shown in phantom line in FIG. 3. With the lights as shown in FIG. 3, the full height of the container 25 will be back-lighted and, in particular, the lower portion of the bottle will be lighted. A vertical strip that is lighted is viewable by a camera 51 mounted opposite the illuminating means. The camera 51, as shown in FIG. 1, has a lens contained within a housing 52. The area of view of the portion of the bottle being inspected is schematically shown by dot-dash lines extending from the lens 52 to the area of the container in FIG. 1. The same pair of dot-dash lines also indicate the area of view of the front portion of the bottle in FIG. 2. It should be pointed out that the camera lens focuses that portion of the front portion of the sidewall of the container that is within its view onto a vertical linear array of pickups within the camera 51. The details of the camera and the electronic processing of the signals resulting from scanning the pickups in the camera is the subject of U.S. application Ser. No. 205,054 of common Assignee with this application.

The vertical array of lamps used to inspect the sidewall characteristics of flint or clear glass containers is provided by the two outer columns of lamps 46 only. By providing a plurality of lamps, the forward wall of the container, which is that portion of the container being viewed by the camera, will have a relatively constant intensity of illumination over its total height and the width of the portion being viewed. In order to ensure that the entire container sidewall is inspected, it is necessary that the container be rotated about its vertical axis through at least 360° of rotation. Rotation of the container about its axis is accomplished by a wheel 53 which has a frictional surface 54, such as a rubber tread.

Figure 3:
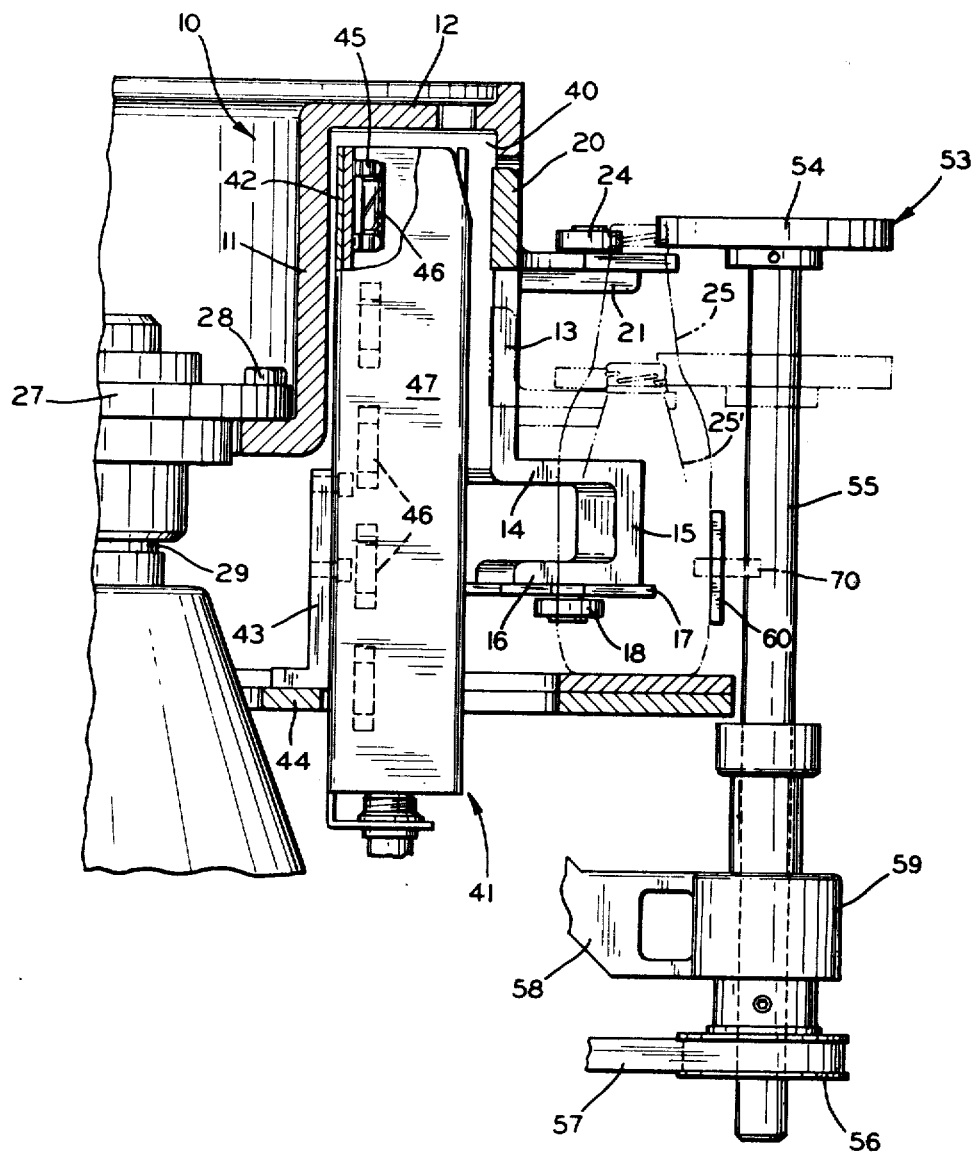
FIG. 3 is a cross-sectional view taken at line 3—3 of FIG. 2.

The wheel is positioned in engagement with the neck of a container when the container is at the location shown in FIGS. 2 and 3. The wheel 54 is mounted on the upper end of a vertical shaft 55. The lower end of the shaft 55, as viewed in FIG. 3, carries a pulley 56 which is driven by a belt 57 in engagement therewith. The means for driving the belt may take the form of an electric motor (not shown). A bracket 58 which carries a bearing 59 serves to support the shaft 55 for rotation about its vertical axis. It should be noted that the shaft 55 and the wheel 53 are biased in the direction of the axis of the bottle in a yielding manner such that when indexing of the starwheel 10 takes place, the neck of the container may pass from engagement with the wheel 53 without undue stress placed thereon. However, it is necessary that the surface of the wheel engage the container neck with sufficient force so as to assure rotation of the container about its vertical axis.

It should be noted that as the containers are moved around from station to station, their bottoms slide on a stationary surface supported by the table 44. To ensure that the bottle, when it is rotated about its vertical axis, is maintained within the confines of the pockets of the starwheel and in the position to be viewed by the camera 51, the side rail 35 is interrupted just in advance of the position where the sidewall inspection is being carried out. An auxiliary portion 60 (See FIG. 2) of the side rail is pivotally mounted to a bracket 61 which in turn is adjustably mounted to a fixed member 62 by a bolt 63 extending through a horizontal slot 64 in the bracket 61. The rail portion 60 is mounted to the bracket 61 by a vertical pivot pin 64. The bracket 61 also carries a stationary ear 65 into which a bolt 66 is threaded. The rail portion 60, at its end opposite the end where the pivot 64 is provided, carries a right angle tab 67 with a portion that overlies the ear 65. The tab 67 has a hole formed adjacent its end and the bolt 66 extends therethrough with clearance from the tab 67. A compression spring 68 extends between the head of the bolt 66 and the tab 67 to, in effect, bias the tab and the one end portion 60 of the side rail into the position shown in FIG. 2. A block 69 is mounted to the side of the tab 67. The outer end of the block 69 carries a roller 70. The roller 70 is therefore biased by the spring 68 through the tab 67 and engages the sidewall of the container being inspected at the position shown in FIGS. 1 and 2. In this way, the container is held at the side near its center of gravity in engagement with the rollers 18.

It should be noted that in FIG. 3, a second dot-dash line configuration is shown for a container with the position of the angle bracket 21, steadying roller 24 and drive wheel 53 moved down to accommodate a shorter container designated 25'. For example, the bottle 25 would represent a 12 oz. beverage bottle such as a beer bottle, while 25' would represent a stubby or short beer or soft drink bottle. While the rollers 70 and rail section 60 are shown in FIG. 3, it should be understood that these are merely shown for purpose of reference, since they normally would not be visible in this view when considering the section line 3—3 designated on FIG. 2.

Figure 6:
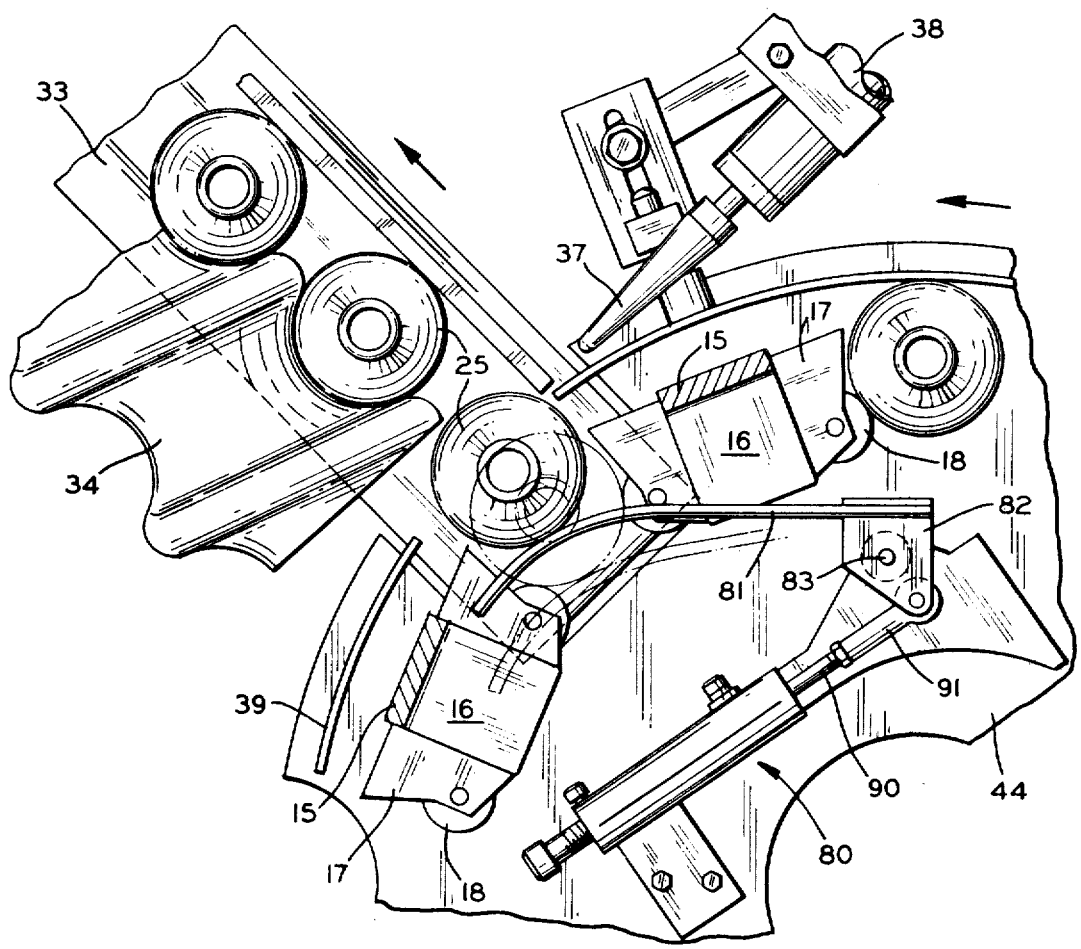
FIG. 6 is a plan view of the exit station of the apparatus of FIG. 1 on an enlarged scale.
Figure 7:
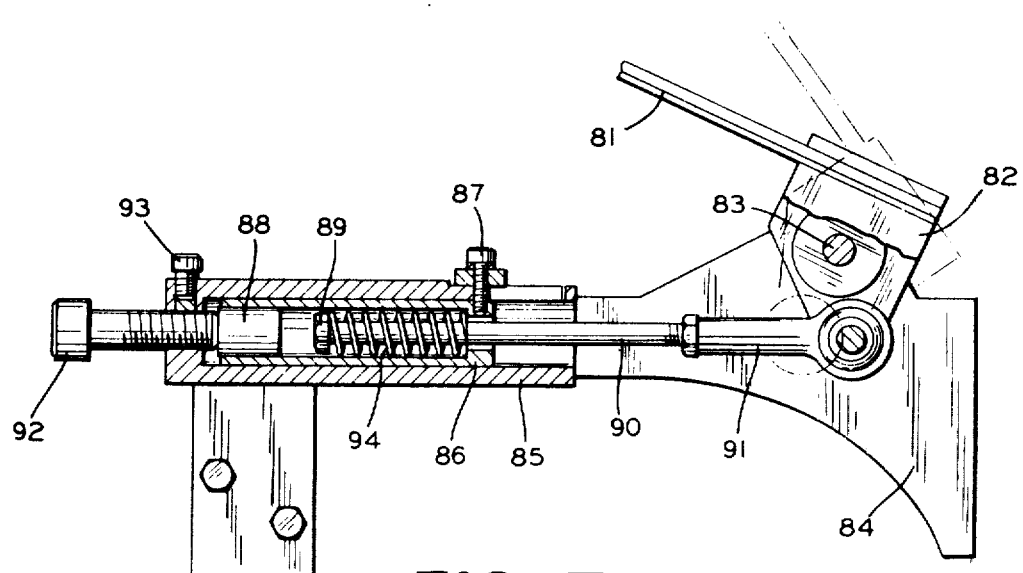
FIG. 7 is an enlarged view, partly in section, of the ejector actuator shown in FIG. 9.

One aspect of the present invention which has led to the design of the starwheel with the arm extension 15 and two horizontal ledges 14 and 16 so as to provide an outwardly extending area, is the provision at the exit position for an improved bottle exit assisting mechanism, generally designated 80, and shown in detail in FIGS. 6 and 7.

FIG. 6 shows the operative position of the assist mechanism and FIG. 7 shows the internal detail of the spring-retaining and biasing means for the assist mechanism. The assist mechanism takes the form of a bent, bottle-engaging member 81. As can be seen, the member 81 extends into the outwardly extending area of the arm bounded by the ledges 14 and 16 and extension 15. Member 81 may be formed of a material which has a non-abrasive surface, yet has a high wear-resistance, for example, a Micarta member formed in the configuration shown and being generally an elongated, rectangular arm. At one end, the member 81 is unrestrained, while at its opposite end it is fixed to a pivoted crank 82. The crank 82 is pivotally supported for rotation about the axis of a pin 83. The pin 83 is supported by a plate 84 which in turn is fixed to the table 44. The plate 84 also supports a cylindrical housing 85 within which a sleeve 86 is coaxially positioned. The sleeve 86 may be adjustably positioned relative to the cylindrical housing 85 by loosening of a threaded bolt 87. The sleeve 86 at one end thereof is provided with a plug 88 which serves as a stop lock against which a head 89 of a rod 90 may engage. The rod 90 is threadably connected to a crank arm 91 which in turn is pivotally connected to the crank 82. A threaded bolt 92 which may be turned in or out of the housing 85 adjustably limits the position of the plug and sleeve 86 within the housing 85. It should be understood that the bolt 87 would be loosened during this adjustment and tightened after the adjustment has been made. A set screw 93 in the cylinder 85 is provided to maintain the adjusted position of the bolt 92, once the position has been selected.

It should be pointed out that with regard to FIG. 6, the member 81, in full line, is shown as being slightly turned in a clockwise direction with respect to the dotted line position illustrated in FIG. 6. The dotted position of the arm in FIG. 7 would correspond to the position of the member 81, were the rod head 89 in actual engagement with the plug 88.

Before a container comes into position at the exit area of the mechanism, shown in FIG. 6, a spring 94 in the sleeve 86 will maintain the head 89 in engagement with the plug 88 and the member 81 will be at its farthest clockwise position with respect to its pivot. As a container is moved into the exit position shown in FIG. 6, the member 81 will first assume the dotted line position, since the container will be biased against the member and the spring 94 will be compressed to a greater extent than that viewed in FIG. 7. Once the container at the exit station is free to move out toward the screw 34, the spring 94 will come into play and assist the container in its exiting movement. However, if the container has been judged or found to have a defect by the gauging and inspection equipment, the plunger 37 will have moved into position to block the exit of the container on the conveyor 33. In this event, the spring 94 will be held in a compressed position and the member 81 will be held in the dotted line position shown in FIG. 6 where it will remain in engagement with the container while it is shifted by indexing the starwheel. The container is held in the starwheel by the rail portion 39. When the bottle has cleared the rail portion 39, it will be discarded by either being pushed from the table 44 or positioned over a cut-out provided in the table, as shown in FIG. 1, with the cut-out overlying the cullet chute 36.

We claim:

1. Apparatus for handling glass containers in spaced apart series into an inspection position in front of an illuminating means with an uninterrupted view of the container from the side thereof opposite the illuminating means and with means to rotate the container while the container is so positioned comprising:
- a generally cylindrical hub, said hub having a horizontally extending periphery which is at a height greater than the height of a container to be inspected;
- means connected to said hub for indexing the hub about its vertical axis;
- a plurality of spaced-apart, downwardly extending arms connected to the periphery of said hub, said arms being of a length sufficient to extend below the center of gravity of a container positioned adjacent thereto;
- container-engaging rollers mounted on said arms at, at least two vertically spaced points, the uppermost rollers located at the finish of the container and said lowermost rollers located below the center of gravity of the container with each arm supporting rollers that are in engagement with the two adjacent containers;
- a peripherally spaced guide rail system extending around said hub adapted to engage containers and maintain them in contact with the rollers;
- means connected to said hub for indexing said hub; and
- means at one of the inspection stations for engaging the finish of the container at said station for rotating the container positioned thereat about its central vertical axis.

2. The apparatus of claim 1 wherein said hub has a plurality of said arms at spaced intervals about the periphery thereof;
- means at one radial location for advancing containers into an area between adjacent arms;
- means at a circumferentially spaced second radial location for moving containers away from between adjacent arms; and
- means at said second location for assisting the movement of containers out from between said arms in a radial direction.

3. The apparatus of claim 2 wherein said means for assisting containers out from between said arms comprises a pivoted arm extending into the path of the container movement into said second location;
- spring-biasing means connected to said pivoted arm for maintaining a force on said pivoted arm; and
- adjustable means limiting the extent of movement of said pivoted arm.

4. The apparatus of claim 1 wherein said downwardly extending arms are formed with a horizontally-extending portion adjacent to which the lower set of rollers are mounted.

5. The apparatus of claim 4 wherein said horizontally extending portion 14 of said arm has a further, lower, inwardly extending portion 16 jointed together by a downward extending portion 15 thereby forming an outwardly extending area in each arm.

6. The apparatus of claim 5, further including first conveyor means for bringing containers into position in contact with said rollers at a loading position, second conveyor means extending generally radially outward from the periphery of said cylindrical hub for moving containers that have been inspected out of said handling system, and means at said second conveyor location for engaging containers at their sidewall and assisting their movement onto said second conveyor.

7. The apparatus of claim 6, further including a container engaging outfeed worm extending along the side of said second conveyor, means for rotating said worm in a direction to move containers away from said hub; and said side-engaging means moving containers into position on said second conveyor to be engaged by said outfeed worm.

8. The apparatus of claim 6, wherein said means at said second conveyor location for engaging containers is positioned at the height of and extends within the outwardly extending area of said arm.

9. The apparatus of claim 1, wherein said guide rail system includes a gap therein opposite said one of the inspection stations, an auxiliary rail member partially spanning said gap, means pivotally supporting one end of said auxiliary rail member on a vertical axis, bottle engaging roller means carried by the opposite end of said rail member, and means biasing said member in the direction of a container in the inspection position to hold the container against said side-engaging rollers.

* * * * *